(12) United States Patent
Hansen et al.

(10) Patent No.: US 11,241,544 B2
(45) Date of Patent: Feb. 8, 2022

(54) HOUSING FOR A MEDICAL INJECTION DEVICE

(71) Applicant: Novo Nordisk A/S, Bagsvaerd (DK)

(72) Inventors: Ken Hansen, Virum (DK); Imran Ghulam, Copenhagen SV (DK); Jesper Bach Noergaard, Virum (DK); Claus Urup Gjoedesen, Copenhagen O (DK); Asger Meng Larsen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 7 days.

(21) Appl. No.: 15/101,730

(22) PCT Filed: Nov. 27, 2014

(86) PCT No.: PCT/EP2014/075811
§ 371 (c)(1),
(2) Date: Jun. 3, 2016

(87) PCT Pub. No.: WO2015/082303
PCT Pub. Date: Jun. 11, 2015

(65) Prior Publication Data
US 2017/0000953 A1     Jan. 5, 2017

(30) Foreign Application Priority Data

Dec. 5, 2013  (EP) .................................... 13195783

(51) Int. Cl.
*A61M 5/315*     (2006.01)
*A61M 5/31*      (2006.01)
(Continued)

(52) U.S. Cl.
CPC ...... *A61M 5/31593* (2013.01); *A61M 5/3129* (2013.01); *A61M 5/31551* (2013.01);
(Continued)

(58) Field of Classification Search
CPC ............ A61M 5/31593; A61M 5/3129; A61M 5/31551; A61M 5/31583;
(Continued)

(56) References Cited

U.S. PATENT DOCUMENTS 2,587,147 A    2/1952  Guion et al.
3,712,301 A    1/1973  Sarnoff
(Continued)

FOREIGN PATENT DOCUMENTS

CN    103442754 A    12/2013
CN    103533975 A     1/2014
(Continued)

OTHER PUBLICATIONS

"Ring", 2020, Merriam-Webster.com Dictionary, Merriam-Webster, https://www.merriam-webster.com/dictionary/ring. (Year: 2020).*
(Continued)

*Primary Examiner* — Brandy S Lee
*Assistant Examiner* — Nidah M Hussain
(74) *Attorney, Agent, or Firm* — Wesley Nicolas

(57) ABSTRACT

The invention relates to a medical injection device having polymeric housing. The housing comprises a moulded outer housing element and a moulded ring-shaped unitary element. The ring-shaped unitary element carries a pointer and a thread segment in predetermined and correlated positions. The pointer points to indicia on a scale drum and the thread segments guides the scale drum. The outer housing element is moulded over the unitary element to form one single component.

2 Claims, 2 Drawing Sheets

(51) Int. Cl.
 B29C 45/14 (2006.01)
 B29L 31/00 (2006.01)
(52) U.S. Cl.
 CPC . *A61M 5/31583* (2013.01); *A61M 2005/3126* (2013.01); *A61M 2207/00* (2013.01); *B29C 45/14* (2013.01); *B29L 2031/7544* (2013.01)
(58) Field of Classification Search
 CPC ...... A61M 2005/3126; A61M 2207/00; A61M 2205/58; A61M 2205/60; A61M 2205/6063; B29C 45/14; B29C 45/16; B29L 2031/7544
 USPC .......................................... 604/189; 264/255
 See application file for complete search history.

(56) References Cited

U.S. PATENT DOCUMENTS

| | | | |
|---|---|---|---|
| 4,822,340 A | 4/1989 | Kamstra | |
| 4,973,318 A * | 11/1990 | Holm | A61M 5/24 604/208 |
| 5,295,965 A | 3/1994 | Wilmot | |
| 6,171,283 B1 * | 1/2001 | Perez | A61M 5/3271 604/181 |
| 6,454,746 B1 | 9/2002 | Bydlon et al. | |
| 6,682,504 B2 | 1/2004 | Nelson et al. | |
| 8,652,387 B2 | 2/2014 | Etter et al. | |
| 8,915,887 B2 | 12/2014 | Avlund | |
| 9,878,102 B2 | 1/2018 | Julian et al. | |
| 9,901,685 B2 | 2/2018 | Pedersen | |
| 10,350,358 B2 | 7/2019 | Schenker et al. | |
| 10,799,644 B2 | 10/2020 | Hansen et al. | |
| 2004/0254543 A1 | 12/2004 | Griffiths | |
| 2005/0241112 A1 | 11/2005 | Worrell | |
| 2007/0176322 A1 * | 8/2007 | Etter | A61M 5/14244 264/255 |
| 2008/0234634 A1 | 9/2008 | Eiland et al. | |
| 2009/0054839 A1 | 2/2009 | Moller et al. | |
| 2012/0053527 A1 | 3/2012 | Cirillo et al. | |
| 2012/0203177 A1 | 8/2012 | Lanier, Jr. et al. | |
| 2012/0289905 A1 * | 11/2012 | Julian | A61M 5/20 604/189 |
| 2012/0300421 A1 | 11/2012 | Askarinya et al. | |
| 2015/0018776 A1 * | 1/2015 | Schenker | A61M 5/2033 604/207 |
| 2015/0080807 A1 * | 3/2015 | Schneider | A61M 5/20 604/189 |
| 2016/0129196 A1 * | 5/2016 | Hirschel | A61M 5/31528 604/211 |
| 2016/0213855 A1 * | 7/2016 | Marsh | A61M 5/20 |
| 2017/0319793 A1 * | 11/2017 | Bergens | A61M 5/31541 |
| 2018/0147363 A1 | 5/2018 | Hansen et al. | |
| 2020/0397997 A1 | 12/2020 | Hansen et al. | |

FOREIGN PATENT DOCUMENTS

| | | |
|---|---|---|
| CN | 104271185 A | 1/2015 |
| CN | 104349806 A | 2/2015 |
| EP | 1603610 A1 | 12/2005 |
| EP | 1819382 A1 | 8/2007 |
| EP | 1909871 | 2/2014 |
| GB | 706620 A | 3/1954 |
| GB | 2325328 A | 11/1998 |
| JP | 2012000146 A | 1/2012 |
| JP | 6543250 B2 | 7/2019 |
| WO | 9810813 | 3/1998 |
| WO | 9938554 | 8/1999 |
| WO | 9938554 A1 | 8/1999 |
| WO | 00/73040 A1 | 12/2000 |
| WO | 0195959 A1 | 12/2001 |
| WO | 02064199 A1 | 8/2002 |
| WO | 2004064902 A1 | 8/2004 |
| WO | 2006045528 A1 | 5/2006 |
| WO | 2007067889 A1 | 6/2007 |
| WO | 2007/107431 A1 | 9/2007 |
| WO | 2008128645 A1 | 10/2008 |
| WO | 2008/148864 A1 | 12/2008 |
| WO | 2010020311 A1 | 2/2010 |
| WO | 2011082272 A2 | 7/2011 |
| WO | 2012046199 A1 | 4/2012 |
| WO | 2012135524 A1 | 10/2012 |
| WO | 2012143437 A1 | 10/2012 |
| WO | 2013110538 A1 | 8/2013 |
| WO | 2013134486 A2 | 9/2013 |
| WO | 2015/017550 A1 | 2/2015 |
| WO | 2015/082303 A1 | 6/2015 |
| WO | 2015082303 A1 | 6/2015 |
| WO | 2015/197629 A1 | 12/2015 |

OTHER PUBLICATIONS

NovoPen® 3, Dial-A-Dose Insulin Delivery System, Novo Nordisk Pharmaceuticals, Inc., 1998.
NovoPen® 3 (Insulin Delivery System), Novo Nordisk Pharmaceuticals, Inc., 1998.

* cited by examiner

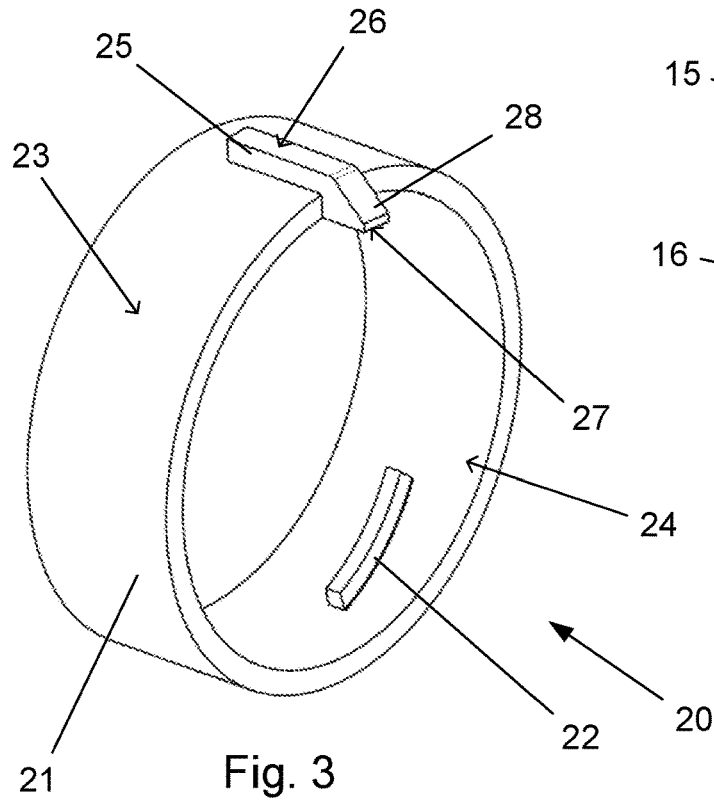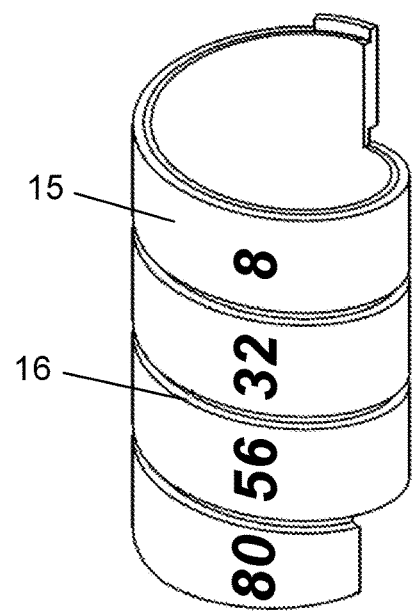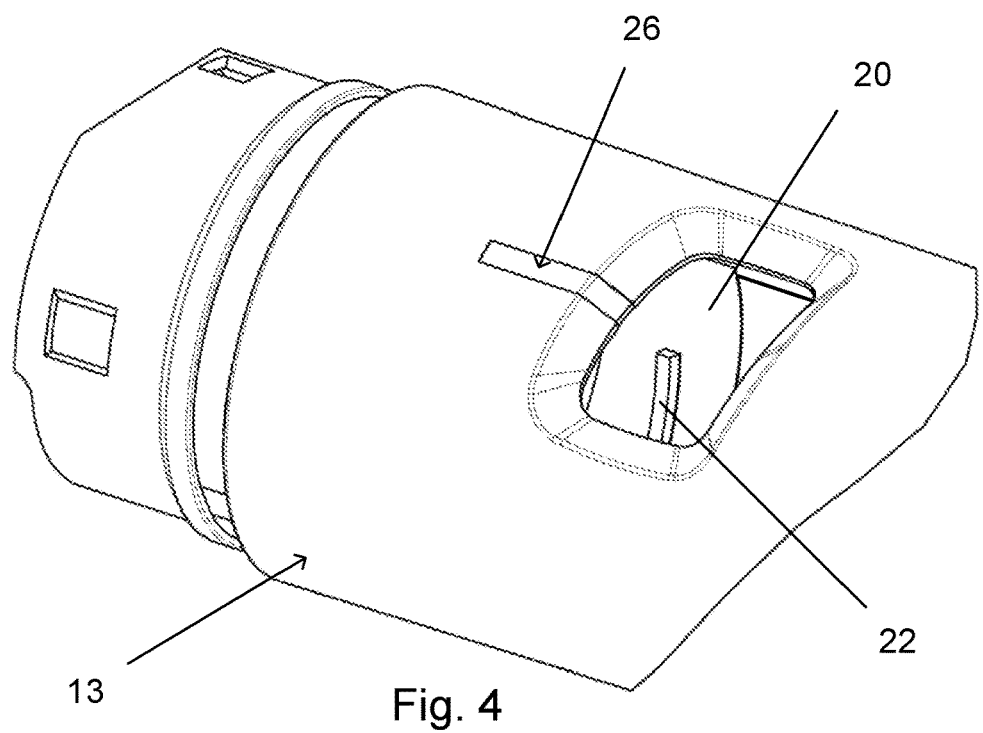

HOUSING FOR A MEDICAL INJECTION DEVICE

CROSS-REFERENCE TO RELATED APPLICATIONS

This application is a 35 U.S.C. § 371 National Stage application of International Application PCT/EP2014/075811 (published as WO 2015/082303), filed Nov. 27, 2014, which claims priority to European Patent Application 13195783.9, filed Dec. 5, 2013.

THE TECHNICAL FIELD OF THE INVENTION

The invention relates to an injection device for injecting set doses of a liquid drug and more precisely to a housing for such injection device moulded from a polymeric material. The invention especially refers to such housing produced by an insert moulding method e.g. 2K moulding.

DESCRIPTION OF RELATED ART

An injection device usually has a housing storing a cartridge containing the liquid drug to be injected. The liquid drug is pressed out from the cartridge through an injection needle by moving a plunger forward inside the cartridge. This forward movement is usually done by a piston rod abutting the plunger which piston rod is moved axially forward by a drive mechanism. The housing is usually made from one or more polymeric components which are usually injection moulded.

An example of such injection device is disclosed in WO 99/38554 (reference is especially made to the FIGS. 15-17, which depicts an injection pen currently sold by Novo Nordisk A/S under the trade name Flexpen®). The proximal housing component is internally provided with a thread which guides a scale drum. The scale drum has a corresponding thread such that the scale drum moves helically out from the housing during rotation. Indicia indicating the various doses a user can select are printed on the scale drum and moves past a window in the housing during rotation. Usually a pointer pointing to the relevant indicia is printed on an external surface of the housing. However, the moulding of internal threads is rather complicated and moulding always involves certain tolerances. Further, the printing also has tolerances. As a result of these tolerances a number of injection devices are missing a correct alignment between the indicia on the scale drum and the pointer printed on the housing.

In EP 1,603,610 the thread in the housing guiding the scale drum is formed only as a segment of a thread, however, the pointer is still printed on the housing.

An example of a moulding method in which a first part is moulded where after a second mould is moulded over the first part is disclosed in US 2005/0241112. Here an indicator element for a polymeric knob is moulded separately where after it is placed in a second cavity. This is followed by a second mould performed in a second cavity to partly cover the indicator element. This technique is commonly recognized as insert moulding.

A similar moulding technique is 2K moulding where the first part and the second part are moulded in the same cavity through different injections points in a sequential process, often using different polymers.

DESCRIPTION OF THE INVENTION

It is thus an object of the present invention to provide an injection device having an improved housing in which the correlation between the indicia on the scale drum and the indicator on the housing is improved.

The invention is defined in claim 1. Accordingly in one aspect the present invention relates to an injection device comprising a polymeric housing. The housing guides a scale drum at least during dose setting such that indicia printed on a rotatable scale drum becomes visible in a window in the housing. Further, a pointer pointing to indicia on the scale drum is provided.

According to the invention, the polymeric housing of the injection device comprises the following two parts:
  a moulded outer housing element, and
  a moulded ring-shaped unitary element carrying a pointer and a thread segment.

The outer housing element is moulded over the ring-shaped unitary element to form one single component referred to as the housing. The ring-shaped unitary element is moulded prior to moulding the outer housing element and is preferably moulded either in another cavity or in the same cavity using a 2K moulding technique. The outer housing element is thus moulded over the unitary element.

The ring-shaped unitary element carries both the pointer and the thread segment guiding the scale drum and the position of the thread segment and the pointer are predetermined and interrelated. In this way the correlation between the pointer and the indicia on the scale drum can be optimized since the alignment between the pointer and the thread segment guiding the scale drum can be set more accurate. The narrow connection between the pointer and the scale drum (via the thread) will ensure a more precise link between the pointer and the scale drum indicia.

The thread segment protrudes inwardly from an inner surface of the ring-shaped unitary element ring and the pointer protrudes outwardly from an outer surface of the ring-shaped unitary element. The outer housing is moulded over the ring-shaped unitary element leaving at least a part, and preferably the outer surface, of the protruding pointer visible for user.

The moulded outer housing element comprises a window, e.g. formed as an opening and the pointer preferably points towards the window such that the protruding pointer directly abuts the window frame. The protruding pointer preferably makes up a part of the window frame and directly abuts with the scale drum, such no element is present between part of the protruding pointer and the scale drum. A user is then able to view the indicia on the scale drum through the window and the pointer points directly to the relevant indicia.

The upper surface of the pointer is usually aligned with the outer surface of the outer housing element and the lower surface of the pointer is aligned with the inner surface of the outer housing element and lies close to the outer surface of the scale drum in order to provide an optimal contrast.

The ring-shaped unitary element and especially the pointer is preferably optical different from the outer surface of the outer housing element such that a user can quickly identify which part is the pointer and which part is the housing. In order to further enhance the contrast, the outer housing element and the ring-shaped unitary element can be moulded from different polymeric materials and/or have different colours.

The finished housing is usually the outer shell of an injection device; however, the housing could also form only part of the outer shell e.g. by being attached to a cartridge-holder carrying the cartridge containing the liquid drug. In an alternative the moulded housing can be surrounded by a thin metal sheet which is then the outer shell.

The scale drum can be any kind of rotatable and axially moving scale drum, the scale drum is preferably provided with an external helical groove or thread such that the resulting movement is helical. In WO 99/38554, the scale drum rotates out from the housing during dose setting. However, in the new generation of spring-driven automatic injection devices as e.g. known from EP 1,909,871, the scale drum moves within the boundaries of the housing both during dose setting and during dose ejection.

The present invention further relates to a method for moulding the polymeric housing of the injection device. The method comprises the steps of:
  (i) moulding a ring-shaped unitary element having an outer surface supporting a pointer and an inner surface supporting a thread segment, and
  (ii) moulding an outer housing element over the unitary element.

The ring-shaped unitary element is moulded prior to moulding the outer housing element and the outer housing element and the unitary element are preferably but not necessarily moulded from different polymeric materials. A preferred moulding technique is 2K moulding in which the unitary element and the outer housing element is moulded in the same cavity using two different injection points. The two moulds are preferably injected sequentially into the cavity.

Further, the outer housing element and the ring-shaped unitary element have different colours.

The present invention thus relate to a medical injection device and preferably to a pen-shaped injection device. The housing of the injection pen preferably has an oblong shape and a circular cross-section and the outer housing element can either form the housing in its entirety or the outer housing can form a part of a larger housing. The injection pen can either be a pre-filled injection device or a durable injection device and in either case it can be a manual driven injection pen or an automatic injection pen.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

"Cartridge" is the term used to describe the container containing the drug. Cartridges are usually made from glass but could also be moulded from any suitable polymer.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

Further the term "injection needle" defines a piercing member adapted to penetrate the skin of a subject for the purpose of delivering or removing a liquid. For many pen systems, the needle cannula of the injection needle comprises a front part for penetrating the skin of the user and a back part for penetrating the septum of the cartridge thus creating a liquid flow between the interior of the cartridge and the subcutaneous layer of the user.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 3 show a perspective view of the unitary element.

FIG. 4 show a perspective view of the housing viewed from outside the housing.

FIG. 5 show perspective view of the scale drum.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the housing element to which the cartridge-holder is attached, whereas the term "proximal end" is meant to refer to the opposite end pointing away from the cartridge-holder and usually carrying the dose dial button.

Figure 1:
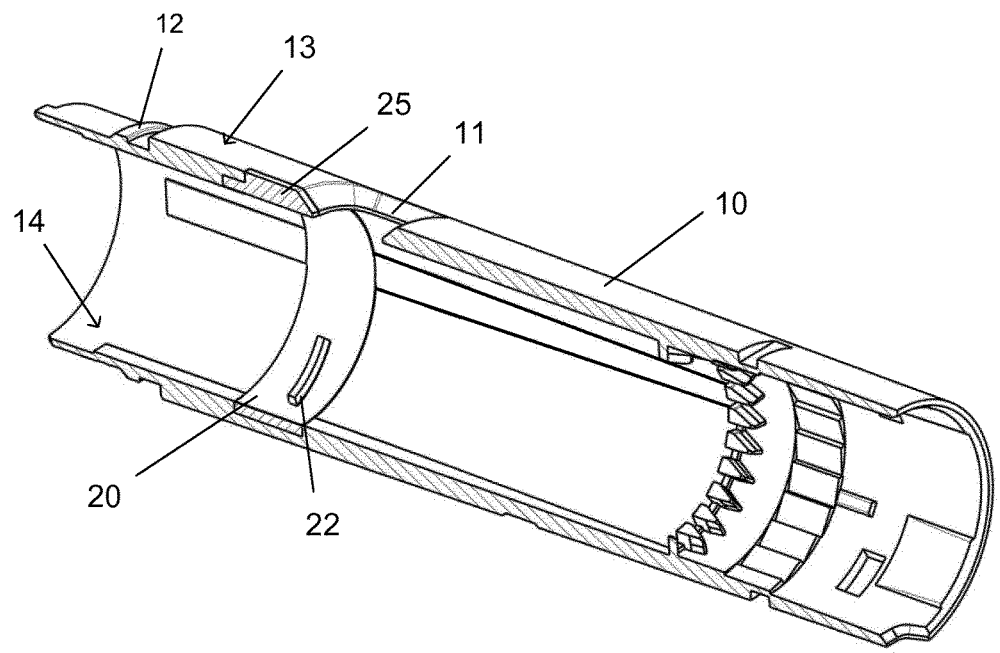
FIG. 1 show a perspective cut-open view of the interior of the housing according to the invention.
Figure 2:
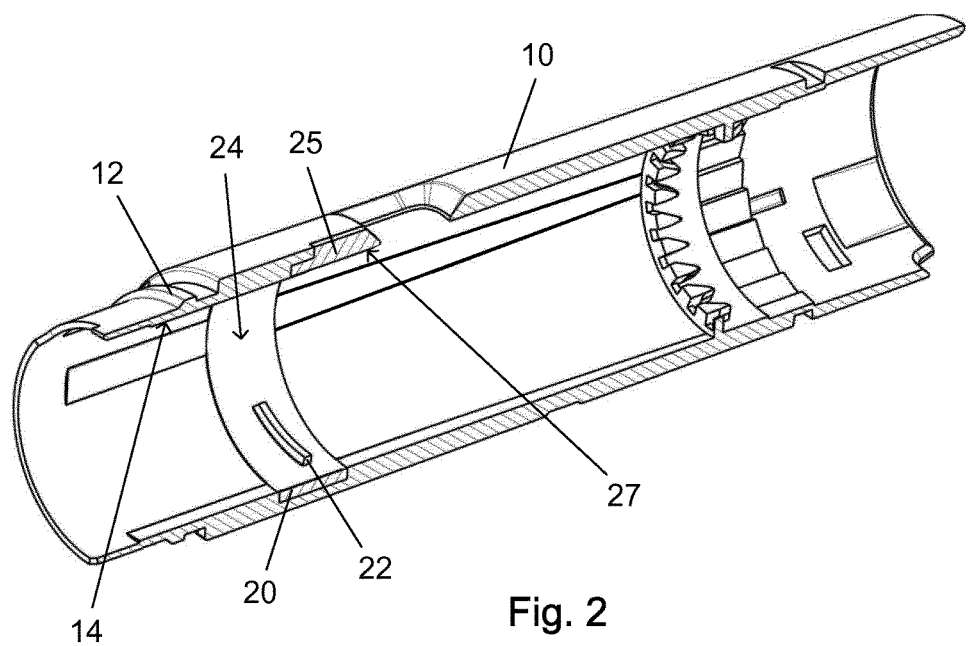
FIG. 2 show the housing according to FIG. 1 viewed from a different angle.

In FIG. 1 the outer housing element is numbered "10" and the unitary element is numbered "20".

The outer housing element 10 is moulded over the unitary element 20 and comprises a window 11 through which a user can view a non-shown scale drum. Proximally the outer housing element 10 is provided with a non-shown dose setting button which a user usually rotates to set a dose. Distally the housing element 10 is provided with a circular ridge 12 which secures a non-shown cartridge-holder. Together the outer housing element 10 and the cartridge-holder make up the housing of an injection device which e.g. could be a pre-filled injection device i.e. an injection device wherein the cartridge-holder is permanently attached to the housing element 10.

When setting a dose, the user rotates the non-shown dose setting button which causes the scale drum 15 to rotate. The scale drum 15 is externally provided with a helical groove or thread 16 which is guided on the thread segment 22 such that the scale drum 15 move in a helical movement whereby indicia printed in a helical row on the outer surface of the scale drum 15 pass by the window 11 in the outer housing element 10 thus indicating the size of the set dose.

The unitary element 20 is depicted in details in FIG. 3. The element 20 is ring-shaped and comprises the ring 21, a thread segment 22 provided internally on the ring 21 and a pointer 25.

The pointer 25 protrude a distance above the outer surface 23 of the ring 21, a distance that makes the outer surface 26 of the pointer 25 to be aligned with the outer surface 13 of the outer housing element 10. Further, the thread segment 22 protrudes beyond the inner surface 24 of the ring 21 thus making it possible for the thread segment 22 to engage the female part of a similar thread in a non-shown scale drum carrying the indicia indicating the size of the set dose. The inner surface 27 of the pointer 25 is aligned with the inner surface 24 of the ring 21 and again with the inner surface 14 of the outer housing element 10. Further, the pointer 25 has a sloping part 28 pointing towards the window 11 of the housing element 10.

The unitary element 20 is first moulded with the pointer 25 and the thread segment 22 in an interrelated and predetermined position, There after the outer housing element 10 is moulded over the unitary element 20. The moulding can be performed as an insert moulding where the unitary element 20 is moulded in a separate cavity or it can be performed as a 2K moulding where the unitary element 20 and the outer housing element 10 is moulded in the same cavity using different injection points.

In the perspective view in FIG. 4 it is shown that the outer surface 26 of the pointer 25 is fully aligned with the outer surface 13 of the housing element 10 after the moulding thus leaving the outer surface 26 of the pointer 25 visible to a user. The scale drum 15 depicted in FIG. 5 is guided on the thread segment 22 via the external groove 16 and the inner surface 27 of the pointer 25 lies very close to the scale drum 15 which provides an extremely fine contrast which can be further enhanced by using different colours of polymers in the moulding process.

Some preferred embodiments have been shown in the foregoing, but it should be stressed that the invention is not limited to these, but may be embodied in other ways within the subject matter defined in the following claims.

The invention claimed is:

1. A method for moulding a polymeric housing for a medical injection device comprising:
   providing a polymeric housing rotatably guiding an axially movable scale drum during dose setting and which the axially movable scale drum having an external helical groove carries indicia viewable through a window provided in the housing, and
   a pointer pointing to the indicia viewable through the window thereby indicating the size of the set dose,
   wherein the polymeric housing comprises:
      a moulded outer housing element, and
      a moulded ring-shaped unitary element comprising at least a portion interior of the outer housing element and moulded prior to moulding the outer housing element, the moulded ring-shaped unitary element moulded with the pointer for indicating the size of a set dose and moulded with a thread segment for guiding the axially movable scale drum wherein the pointer and the thread segment are moulded in an interrelated and predetermined position,
   wherein the ring-shaped unitary element comprises an inner surface from which the thread segment protrudes inwardly to engage the helical groove of the axially movable scale drum and an outer surface from which the pointer protrudes outwardly, and wherein,
   the moulded outer housing element is injection moulded over the ring-shaped unitary element leaving at least a part of protruding pointer visible,
   wherein an outer surface of protruding pointer is aligned with an outer surface of the housing element and protruding pointer forms part of the window provided in the housing, and
   wherein the outer housing element and the unitary element have different colours,
   wherein the method comprises the steps of:
      moulding a ring-shaped unitary element having an outer surface from which the pointer protrudes outwardly and an inner surface from which surface the thread segment protrudes inwardly, moulding an outer housing element over the unitary element, and wherein the unitary element is moulded prior to moulding the outer housing.

2. The method for moulding a polymeric housing according to claim 1, wherein the outer housing element and the unitary element are moulded from different polymeric materials.

\* \* \* \* \*